(12) United States Patent
Bucci et al.

(10) Patent No.: US 10,105,669 B2
(45) Date of Patent: Oct. 23, 2018

(54) TAPERED FLUIDIZED BED REACTOR AND PROCESS FOR ITS USE

(71) Applicant: Hemlock Semiconductor Corporation, Hemlock, MI (US)

(72) Inventors: John V. Bucci, Midland, MI (US); Raymond Anthony Cocco, Elmhurst, IL (US); Max E. Dehtiar, Saginaw, MI (US); Patrick J. Harder, Saginaw, MI (US); S. B. Reddy Karri, Naperville, IL (US); Ted M. Knowlton, Willowbrook, IL (US); Michael J. Molnar, Freeland, MI (US)

(73) Assignee: HEMLOCK SEMICONDUCTOR OPERATIONS LLC, Hemlock, MI (US)

( * ) Notice: Subject to any disclaimer, the term of this patent is extended or adjusted under 35 U.S.C. 154(b) by 782 days.

(21) Appl. No.: 14/423,271

(22) PCT Filed: Aug. 26, 2013

(86) PCT No.: PCT/US2013/056611
§ 371 (c)(1),
(2) Date: Feb. 23, 2015

(87) PCT Pub. No.: WO2014/035878
PCT Pub. Date: Mar. 6, 2014

(65) Prior Publication Data
US 2015/0217252 A1    Aug. 6, 2015

Related U.S. Application Data

(60) Provisional application No. 61/694,449, filed on Aug. 29, 2012, provisional application No. 61/794,320, filed on Mar. 15, 2013.

(51) Int. Cl.
*G01N 31/00* (2006.01)
*B01J 8/24* (2006.01)
(Continued)

(52) U.S. Cl.
CPC ............... *B01J 8/24* (2013.01); *B01J 8/1827* (2013.01); *B01J 8/1836* (2013.01); *B01J 8/1872* (2013.01);
(Continued)

(58) Field of Classification Search
CPC . B01J 8/24; B01J 8/1836; B01J 8/1872; B01J 8/0045; B01J 8/1827
(Continued)

(56) References Cited

U.S. PATENT DOCUMENTS

| | | | |
|---|---|---|---|
| 4,032,407 A | 6/1977 | Scott et al. | |
| 4,092,446 A | 5/1978 | Padovani et al. | |

(Continued)

FOREIGN PATENT DOCUMENTS

| | | |
|---|---|---|
| DE | 839688 C | 5/1952 |
| EP | 0088638 B1 | 9/1985 |

(Continued)

OTHER PUBLICATIONS

Cadoret L. et al.: "Silicon Chemical Vapor Deposition on Macro and submicron powders in a fluidized bed", Powder Technology, Elsevier Sequoia, Lausanne, Ch. vol. 190, No. 1-2, Mar. 5, 2009; 4 pages.
(Continued)

*Primary Examiner* — An Do
(74) *Attorney, Agent, or Firm* — Cantor Colburn LLP

(57) ABSTRACT

A fluidized bed reactor includes a gas distributor, a tapered section above the gas distributor, and an expanded head above the tapered section. The gas distributor defines a plurality of inlets surrounding a product withdrawal tube, which extends away from the fluidized bed reactor. The
(Continued)

fluidized bed reactor is useful in a process for fluidizing relatively large particles, such as Geldart Group B particles and/or Geldart Group D particles, where said particles are in a bubbling fluidized bed residing, in whole or in part, in the tapered section. The fluidized bed reactor and process may be used for manufacturing polycrystalline silicon.

8 Claims, 4 Drawing Sheets

(51) Int. Cl.
*B01J 8/18* (2006.01)
*B01J 8/44* (2006.01)
*C01B 33/027* (2006.01)
*C01B 33/03* (2006.01)
*G01N 15/02* (2006.01)

(52) U.S. Cl.
CPC ............... *B01J 8/44* (2013.01); *C01B 33/027* (2013.01); *C01B 33/03* (2013.01); *G01N 15/0255* (2013.01); *B01J 2208/00672* (2013.01); *B01J 2208/00752* (2013.01); *B01J 2208/00761* (2013.01); *B01J 2208/00902* (2013.01); *B01J 2208/00938* (2013.01); *B01J 2208/00982* (2013.01); *B01J 2208/00991* (2013.01)

(58) Field of Classification Search
USPC ................ 702/22, 29, 30; 422/129, 139
See application file for complete search history.

(56) References Cited

U.S. PATENT DOCUMENTS

| | | | |
|---|---|---|---|
| 4,207,360 A | 6/1980 | Padovani | |
| 4,213,937 A | 7/1980 | Padovani et al. | |
| 4,288,162 A | 9/1981 | Sakamoto et al. | |
| 4,424,199 A | 1/1984 | Iya | |
| 4,585,673 A | 4/1986 | Sigai | |
| 4,748,052 A | 5/1988 | Allen | |
| 4,825,124 A | 4/1989 | Sigai | |
| 4,851,297 A | 7/1989 | Allen et al. | |
| 4,868,013 A | 9/1989 | Allen | |
| 4,952,425 A | 8/1990 | Allen et al. | |
| 4,993,264 A | 2/1991 | Cody et al. | |
| 5,011,285 A | 4/1991 | Jorgensen et al. | |
| 5,015,528 A | 5/1991 | Pinneo | |
| 5,022,268 A | 6/1991 | Wolf et al. | |
| 5,165,908 A | 11/1992 | Van Slooten et al. | |
| 5,175,942 A | 1/1993 | Dutta et al. | |
| 5,675,071 A * | 10/1997 | Cody ............... B01J 8/001 73/19.03 |
| 5,798,137 A | 8/1998 | Lord et al. | |
| 5,810,934 A | 9/1998 | Lord et al. | |
| 6,541,377 B2 | 4/2003 | Kim et al. | |
| 7,001,579 B2 | 2/2006 | Metzger et al. | |
| 7,584,919 B2 | 9/2009 | Adler et al. | |
| 7,927,984 B2 | 4/2011 | Molnar | |
| 7,935,327 B2 | 5/2011 | Arvidson et al. | |
| 8,435,452 B2 * | 5/2013 | Wyatt, Jr. ............ B01J 8/125 208/106 |
| 8,580,203 B2 | 11/2013 | Jung et al. | |
| 2008/0187481 A1 | 8/2008 | Ibrahim et al. | |
| 2009/0047204 A1 * | 2/2009 | Kim ................ C01B 33/027 423/349 |
| 2009/0324479 A1 | 12/2009 | Kulkarni et al. | |
| 2011/0158888 A1 | 6/2011 | Erk | |
| 2011/0244124 A1 | 10/2011 | Kulkarni et al. | |

FOREIGN PATENT DOCUMENTS

| | | |
|---|---|---|
| EP | 0684871 B1 | 5/1998 |
| EP | 0832312 B1 | 1/2003 |
| EP | 1924349 B1 | 1/2010 |
| JP | S58204814 A | 11/1983 |
| JP | S58213623 A | 12/1983 |
| JP | S5945917 A | 3/1984 |
| JP | S605013 A | 1/1985 |
| JP | 840717 | 2/1996 |
| KR | 20120095755 A | 8/2012 |
| KR | 1020140013550 A | 2/2014 |
| TW | 201136830 A1 | 11/2011 |
| WO | 9011858 | 10/1990 |
| WO | 9641036 A2 | 12/1996 |
| WO | 2010053659 A1 | 5/2010 |
| WO | 2010031099 A1 | 7/2010 |
| WO | 2012090131 A1 | 7/2012 |

OTHER PUBLICATIONS

Daleffe R V et al.: "Analysis of the effect of particle size distributions on the fluid dynamic behavior and segregation patterns of fluidized, vibrated and vibrofluidized beds", Asia-Pacific Journal of Chemical Engineering; Jan. 2007; 3 Pages.
International Search Report for International Application No. PCT/US2013/056611; dated Aug. 26, 2013; 6 pages.
Korean Patent No. 10-2014 0013550; Date of Publication: Feb. 5, 2014; Machine Translation; 11 pages.
Taiwanese Patent Application 201136830; Date of Publication: Nov. 1, 2011; Abstract Only; 1 page.
Chew et al., "Axial Segregation in Bubbling Gas-Fluidized Beds with Gaussian and Lognormal Distributions of Geldart Group B Particles"; AIChE Journal, 2010, vol. 56, pp. 3049-3061.
Darton et al., "Bubble Growth Due to Coalescence in fluidised Beds"; Trans. IChemE, 1977, vol. 55, pp. 274-280.
Davies et al., "Particle size monitoring in a fluidized bed using pressure fluctuations", Powder Technology, vol. 180, 2008, pp. 307-311.
Du, J. et al., Modeling and control of particulate processes and application to polysilicon production, Chemical Engineering Science, vol. 67, 2012, pp. 120-130.
Zenz et al., "Fluidization and Fluid-Particle Systems"; Reinhold Publishing, 1960, pp. 256-257.
Filtvedt et al., "Chemical vapor deposition of silicon from silane: Review of growth mechanisms and modeling/scaleup of fluidized bed reactors"; Solar Energy Materials & Solar Cells 2012, Vol, 107, pp. 188-200.
German Patent No. 839688; Date of Publication: May 23, 1952; Machine Translation; 5 pages.
Japanese Patent No. 840717; Date of Publication: Feb. 13, 1996; Machine Translation; 6 pages.
Japanese Patent No. S58204814; Date of Publication: Nov. 29, 1983; Abstract; 2 pages.
Japanese Patent No. S58213523; Date of Publication: Dec. 12, 1983; Abstract; 2 pages.
Japanese Patent No. S5945917: Date of Publication: Mar. 15, 1984; Abstract; 2 pages.
Japanese Patent No. S605013; Date of Publication: Jan. 11, 1985; Abstract; 2 pages.
Korean Patent No. 20120095755; Date of Publication: Aug. 29, 2012; Abstract; 1 page.
Kunii et al., "Fluidization Engineering"; Butterworth-Heinemann Publishers, 1991, pp. 65-67, 76-79, 88-90, 165-169, 173-183.
Ridgway, K., "The Tapered Fluidised Bed—A New Processing Tool"; Chemical and Process Engineering, 1965, Vo. 6, pp. 317-321.
Masayuki Norio et al., "A New Similarity Rule for Fluidized Bed Scale-Up"; AIChE Journal vol. 32, No. 9; Sep. 1986; 17 pages.

\* cited by examiner

TAPERED FLUIDIZED BED REACTOR AND PROCESS FOR ITS USE

This is the U.S. national stage of application No. PCT/US2013/056611, filed on Aug. 26, 2013. Priority under 35 U.S.C. § 119(a) and 35 U.S.C. § 365(b) is claimed from U.S. Patent Application Ser. No. 61/694,449, filed Aug. 29, 2012, and U.S. Patent Application Ser. No. 61/794,320, filed Mar. 15, 2013, the disclosures of which are incorporated herein by reference.

BACKGROUND OF THE INVENTION

A process for making polycrystalline silicon may include feeding gases comprising hydrogen and a silicon monomer (such as $HSiCl_3$ or $SiH_4$) to a fluidized bed containing silicon particles that are maintained at high temperature. The particles grow in size, and when large enough, are passed out the bottom of the fluidized bed reactor (FBR) as product. The vent gases exit the top of the FBR. The vent gas stream can be passed through a recovery process where condensations, scrubbing, absorption and adsorption are unit operations often used to facilitate the capture of silicon monomer and hydrogen for recycle.

One problem with the FBR process is that the wall surrounding the bed of silicon particles must be heated to a temperature higher than the average bed temperature to facilitate heat transfer. That can be done, for example, by use of resistance heating, microwave energy, radio frequency inductive heating, or infrared radiation. All heating methods have unique operating problems. One problem, however, is that the bottom of the FBR may be hot, and the feed gas is reactive when it contains $HSiCl_3$ and hydrogen. As a result, the feed gas distributor, clusters of large particles, especially those in regions where agitation is less active and particles are in contact for prolonged periods of time, and reactor side walls are prone to rapid deposition of silicon. Those deposits subsequently disrupt the proper feed distribution, product separation, and heat transfer of the system.

Another problem with the FBR process is that slugging can occur in a cylindrical FBR because bubbles grow quickly in fluidized beds containing relatively large particles. "Slugging" refers to formation of gas bubbles that are so large that they disrupt fluidization and reduce yield. Typically, these bubbles can reach a diameter close to a diameter of the vessel. The act of slugging leads to significant pressure fluctuations in the system and uneven forces on the vessel wall. Since the fluctuation behavior is dynamic with bubbles growing in size and breaking apart at the freeboard, the preferred approach for characterizing its magnitude is the time series-average of the standard deviation of pressure fluctuations. The standard deviation of pressure fluctuations is proportional to the excess gas velocity and hence a measure of aggregate bubble size for the largest bubbles formed in the system. These forces manifest themselves with measurable vibrations, and tools exist in the art to measure such vibrations in the field. For instance, the pressure drop across the entirety or a section of the fluidized bed can be measured using differential pressure transducers.

A third challenge with silicon deposition fluidized bed reactors is the delivery of energy into the process to support the deposition chemistry if the wall is the primary mode of transport. As diameter of a cylindrical FBR increases, the wall perimeter of the FBR increases linearly and hence the wall surface area per unit length increases linearly, but the heat requirement for operation increases with the square of diameter of the FBR at a given average superficial velocity. To accommodate for this change, either the heat flux needs to increase or the bed height must increase to achieve the necessary delivery of energy. The maximum heat flux from the wall to the bed can be limited by the allowable thermal stress associated with the wall material of construction and heat delivery method. Internal heaters and heat exchangers have been proposed in the art to supplement energy input, but these add complexity not to mention challenges with maintaining product purity. Height is also limited by growth of bubbles for some fluidization processes. With limitations on heat flux, increases to the FBR diameter result in larger height, but bubble growth rate increases resulting from more bed level can lead to excessive slugging in the FBR. This makes it difficult to scale up an FBR process into a commercially viable producer of polycrystalline silicon.

Polycrystalline silicon particles made in fluidized bed reactors generally fall into Geldart Group B and/or Geldart Group D classification. The Geldart Classification Scale refers to the collective behavior of particles in fluidized bed reactors, and distinct regimes of this solid behavior can be characterized from the average particle size and the relative densities of the solid and fluid phases. For instance, the appropriate averaging description for the particle size distribution that adequately quantifies the drag behavior of a gas-particle system is the surface-to-volume mean or Sauter mean particle diameter. This metric shows the influence of gas-solid drag from the smaller particles on the overall population which helps move larger beads. For silicon particles, Geldart Group B particles may have particle diameters ranging from 200 to 800 micrometers. Geldart Group B particles exhibit formation of bubbles at the onset of fluidization, which continue to grow from the point of injection. The bubble size can be large, e.g., on the order of feet in some cases. For the silicon deposition FBR processes, samples of industrially available material show particle size distributions to fall within the Geldart B range, typically 700-800 micrometers.

Geldart Group D particles have the largest particle diameters of all Geldart groups. Gas requirements for fluidization of Geldart Group D particles are larger than Group B particles and bubble growth is also faster. During fluidization, Geldart Group B and Geldart Group D particles have enormous bubble diameters, and spouting and/or slugging are commonly observed in large, cylindrical fluidized beds. Due to the problems of slugging, Geldart Group D particles are typically processed in spouting beds where gas requirements are less than needed in bubbling fluidized beds, but use of a central feed jet limits the efficiency of gas-solids contact. Alternatively, a method to reduce bubble growth within bubbling fluidized beds is to induce breakage of bubbles within the bed. While mechanical solutions such as baffles can be used to break bubbles, in the polysilicon deposition application, implementation of a robust, erosion-resistant baffle design that likewise doesn't induce contamination of product is difficult.

A fourth complexity of silicon deposition fluidized bed reactors is the tendency to produce fines (on the order of 1 micrometer particle size) within the reaction system that entrain out of the reactor. Chemistry within the bubble phase is also known to facilitate nucleation reactions that create the fine silicon powders. A common method to limit this problem is to shrink the average particle size within the bed to limit growth of bubbles. Smaller particles however have a higher likelihood of contamination risk. Alternatively, fluidized bed deposition reactors can be operated in series but this requires more capital investment.

There is a need in the polycrystalline silicon industry to improve FBR technology to address these problems.

BRIEF SUMMARY OF THE INVENTION

A fluidized bed reactor (FBR) comprises a gas distributor, a tapered section above the gas distributor, and an expanded head above the tapered section. The FBR may be used in a process for making polycrystalline silicon.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE INVENTION

Figure 1:
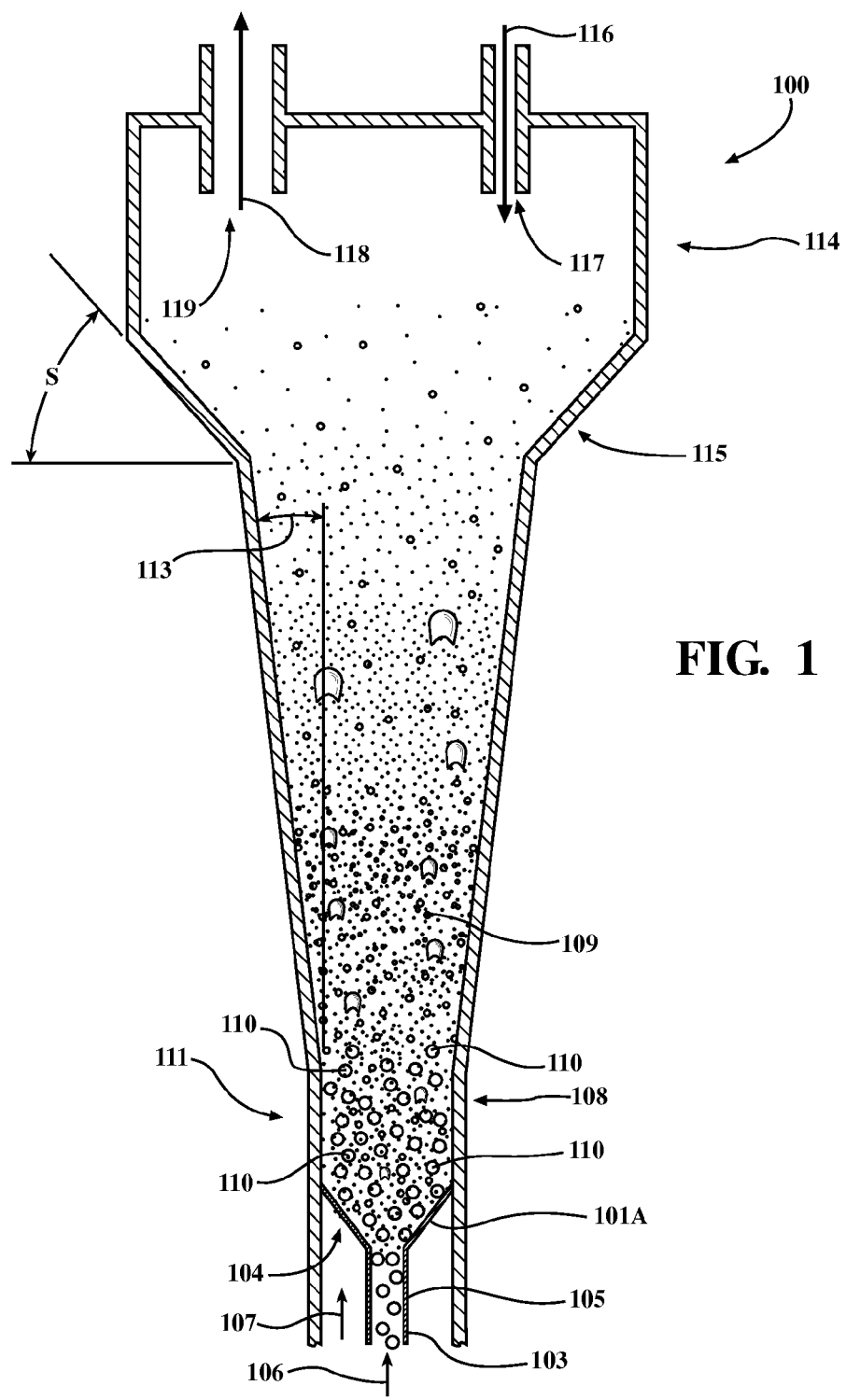
FIG. 1 shows a cross section of a fluidized bed reactor (FBR) 100.

The Brief Summary of the Invention, the Brief Description of the Drawings, and the Abstract are hereby incorporated by reference.

Definitions and Usage of Terms

All amounts, ratios, and percentages are by weight unless otherwise indicated. The articles 'a', 'an', and 'the' each refer to one or more, unless otherwise indicated by the context of specification. The disclosure of ranges includes the range itself and also anything subsumed therein, as well as endpoints. For example, disclosure of a range of 2.5 to 10.0 includes not only the range of 2.5 to 10.0, but also 2.7, 2.9, 3.4, 4.5, 6.7, 7.4, 9.3, and 10.0 individually, as well as any other number subsumed in the range. Furthermore, disclosure of a range of, for example, 2.5 to 10.0 includes the subsets of, for example, 2.6 to 3.5, 3.0 to 3.4, 2.6 to 3.7, 3.8 to 4.0, 4.0 to 5.0, 4.5 to 6.5, and 7.0 to 10.0, as well as any other subset subsumed in the range. Similarly, the disclosure of Markush groups includes the entire group and also any individual members and subgroups subsumed therein. For example, disclosure of the Markush group monochlorosilane, dichlorosilane, trichlorosilane, tetrachlorosilane, hexachlorodisilane, and pentachlorodisilane includes the member trichlorosilane individually; the subgroup trichlorosilane and tetrachlorosilane, and any other individual member and subgroup subsumed therein.

For purposes of this application, the term 'chlorosilanes' refers to any silane species having one or more chlorine atoms bonded to silicon and includes, but is not limited to monochlorosilane ($H_3SiCl$), dichlorosilane ($H_2SiCl_2$), trichlorosilane ($HSiCl_3$), tetrachlorosilane ($SiCl_4$), and various chlorinated disilanes such as hexachlorodisilane and pentachlorodisilane. For the purposes of this application, the term 'bromosilanes' refers to any silane species having one or more bromine atoms bonded to silicon and includes, but is not limited to monobromoosilane ($H_3SiBr$), dibromosilane ($H_2SiBr_2$), tribromosilane ($HSiBr_3$), tetrabromosilane ($SiBr_4$), and various brominated disilanes such as hexabromodisilane and pentabromodisilane. Additionally, the term 'silicon monomer' refers to any silane species having one silicon atom per molecule (e.g., silane, or $HSiCl_3$, or a combination of $HSiCl_3$ and $SiCl_4$).

FBR Design

A fluidized bed reactor (FBR) comprises:
a. a gas distributor having an outer edge,
   i. a product withdrawal tube mounted to the gas distributor,
   ii. a plurality of feed inlets defined by the gas distributor between the outer edge and the product withdrawal tube;
b. a tapered section above the gas distributor, where the tapered section of the FBR expands upward and outward from the outer edge of the gas distributor; and
c. a head above the tapered section.

Gas Distributor

The gas distributor or grid defines a plurality of feed inlets. The feed inlets are located between the outer edge of the gas distributor and the product withdrawal tube, which is mounted to the gas distributor and extends away from the FBR. The gas distributor may have at least 2 feed inlets. Alternatively, the gas distributor may have at least 4 feed inlets. The product withdrawal is used to remove larger diameter particles (product) from the FBR. One or more product withdrawal tubes may be mounted to the gas distributor. The gas distributor may further define a plurality of gas inlets located between the feed inlets and the outer edge.

The gas distributor used in the FBR may have a conical shape. The conical gas distributor has a diameter that has a maximum at the outer (top) edge and decreases going downward. The product withdrawal tube may be located at the lowermost portion of the conical gas distributor. One or more product withdrawal tubes may be mounted to the conical gas distributor. Alternatively, one product withdrawal tube may be mounted to the lowest portion of the conical gas distributor.

Inlets can be vertical, horizontal, angled, or combinations thereof. The gas distributor may optionally be cooled through use of a contained liquid cooling channel. Suitable liquids include water or industrial heat transfer fluids. For example, the liquid may be a polydimethylsiloxane-based silicone fluid.

The better the mixing at the bottom of the bed, the hotter the gas distributor gets. This can cause deposition on the distributor, which is undesirable and can plug up the holes. Cooling the gas distributor minimizes this. See Kulkarni et al. in US application 2011/0244124 A1 for local cooling of gas distributor description.

Optional Lower Straight Section Above Gas Distributor and Below Tapered Section The FBR optionally further comprises a lower straight section above the gas distributor. The lower straight section has a vertical wall and may have a cylindrical shape. The ratio of height to diameter (L/D ratio) is typically 0.5 or less in the cylindrical lower straight section. During operation of the FBR, a portion of a bubbling fluidized bed may reside in the lower straight section, when the lower straight section is present. Segregation may occur in the lower straight section, i.e., the larger diameter particles (product) may preferentially segregate from smaller diameter particles (e.g., seed and intermediately sized particles) in the lower straight section, and the product moves downward through the lower straight section to exit the FBR through the product withdrawal tube. Segregation can only occur if the superficial velocity is above minimum fluidization velocity but below the transition velocity that induces higher mixing, which is typically 30-50% higher than minimum fluidization velocity. Heat input into this section of the reactor must also be managed relative to the gas flow rate and inlet gas temperature to avoid excessive temperatures near the wall, which would encourage localized sintering resulting from deposition reactions and potential interruptions to the flow path from the gas distributor below. Typically, for a chlorosilane/hydrogen mixture, a process temperature below 500° C. is sufficient to limit deposition. Likewise, control of the vapor composition near the wall by injecting an etching gas can also limit the risk of deposition-induced sintering.

Tapered Section

The tapered section of the FBR expands upward and outward from the outer edge of the gas distributor (or from the top of the lower straight section, when the lower straight section is present). The cone angle at which the tapered section expands upward and outward may range from 2.5° to 10.0° from vertical. Alternatively, the cone angle may range from 3.5° to 7.0°, alternatively 4.0° to 10.0°, alternatively 4.0° to 7.0°, and alternatively 4.0° to 5.0°.

Without wishing to be bound by theory, it is thought that because the tapered section has a higher surface area (i.e., higher than a cylindrical fluidized bed reactor with the same height and the diameter of the gas distributor would have), including the tapered section will improve heat transfer capability. The cone angle of the tapered section also reduces bubble growth rate and slugging (as compared to the cylindrical fluidized bed reactor), so height and diameter of a FBR with a tapered section can be greater than those of a cylindrical fluidized bed reactor.

At least a portion of the bubbling fluidized bed resides in the tapered section of the FBR when the FBR operates. The FBR further comprises a heater oriented so as to provide heat to the tapered section when the heater operates.

The tapered section can also have injection points for additional gas flow above the primary gas distributor. As superficial velocity in the bed is increased, there comes a point where bubbles in the bottom of the bed grow to the point of slugging. Staging of the gas flow allows for more gas volume throughput in the bed as well as more stable motion at higher bed inventories. This gas can be fresh feed gas to facilitate additional reaction throughput, etching gas such as silicon tetrachloride, or diluent gas such as hydrogen. For gas mixtures having the chemical potential to form silicon under process conditions, the discharge port of gas injection may require cooling to prevent localized silicon build up at the discharge point.

Optional Upper Straight Section Above Tapered Section and Below Head

The FBR may optionally further comprises an upper straight section above the tapered section. The upper straight section has a vertical wall and may have a cylindrical shape. The height of the upper straight section depends on various factors including the size of the tapered section and the silicon bearing source gas selected. Generally, the upper straight section exceeds a transport disengagement height of the FBR, and is useful for preventing particles from exiting the top of the FBR. Calculation of the transport disengagement height is described in the literature. For example, as the particles become fluidized, the particles may be entrained in the silicon bearing source gas. Generally, with appropriately sized seed particles, entrainment of the bed particles ceases before the particles exceed the transport disengagement height although very small particles such as those resulting from attrition and nucleation processes can still be entrained. Therefore, the upper straight section of the FBR extends beyond the transport disengagement height to prevent the particles that are entrained within the silicon bearing source gas from escaping the FBR.

Head

The head of the FBR is mounted above the tapered section (or above the upper straight section, when it is present). The head may be an expanded head (i.e., the expanded head) has a diameter larger than the diameter of the top of the tapered section. The head does not need to have a larger diameter than the top of the tapered section when the bubbling fluidized bed level does not exceed conditions where the fluidization velocity drops below minimum fluidization velocity (Umf). However, transitioning to an expanded head may be more suitable for managing overall entrainment in the polysilicon application since typical fines capture and recycle devices such as cyclones can induce contamination sources for the product. The expanded head is sufficiently large in diameter plus has enough transport disengagement height above where it has its maximum diameter to keep seed particles in the bubbling fluidized bed. Typically, gases laden with solids expand with a jet cone angle of approximately 22 degrees. However, the angle of the conical expansion cannot be unduly large since if it is too flat, silicon particles can build up at the base of the expanded head. The angle at which the head expands depends on various factors including whether transport disengagement height extends into the expanded head (e.g., whether the upper straight section is present), and the friction properties of the particles in the FBR. For irregularly shaped-silicon seed particles, a slope S of the expanded head with respect to the horizontal plane of the transition point should be at least 40 degrees to allow solids to slide back into the system.

The head has a particle inlet for adding seed particles to the FBR. The seed particles (e.g., seed particles of silicon) are a raw material on which material is deposited in the bubbling fluidized bed to make the larger diameter particles (product). The head also has a gas outlet at or near the top. A sintered metal filter may optionally be provided in the gas outlet. Without wishing to be bound by theory, the sintered metal filter may allow removal of fine silicon particles from the effluent gas for subsequent reprocessing methods such as use as silicon feedstock for new silane intermediates or treatment via compaction to form cakes.

Heater

The FBR described above further comprises a heater oriented so as to provide thermal energy to the tapered section when the heater operates. As defined the heater is any appropriate energy delivery source that can be used to heat the gases and bed to the desired temperature necessary to support chemical vapor deposition. This may include but not be limited to serpentine resistance heaters or induction coils. The FBR may optionally further comprise one or more additional heaters surrounding sections of the reaction chamber. For example, the FBR may further comprise a supplemental heater oriented to the FBR so as to provide heat at the gas distributor when the supplemental heater operates. Alternatively, the FBR may further comprise a section heater oriented to the FBR, so as to provide heat to at least one straight section when the section heater operates. Alternatively, the FBR may have both a supplemental heater and one or more section heaters.

Process

The FBR described above may be used in a process for making polycrystalline silicon. In this process, gases comprising hydrogen and a silicon bearing source gas are fed into a bubbling fluidized bed containing silicon particles. At least a portion of the bubbling fluidized bed resides in the tapered section of the FBR, which has a cone angle from the vertical, as described above. Without wishing to be bound by theory, it is thought that the benefit of this operation is slowing of the rate of bubble growth in the FBR as it leaves the gas distributor (relative to a fluidized bed reactor process where the bubbling fluidized bed resides in a cylindrical vessel).

Silicon particles (seed particles of silicon) are fed into the FBR above the tapered section, e.g., through the particle inlet on the expanded head of the FBR.

The silicon bearing source gas is fed into the FBR through the feed inlets defined by the gas distributor. All, or a portion, of the hydrogen may be fed into the FBR through the feed inlets in addition to the silicon bearing source gas. As the chemistry proceeds to deposit silicon, the particles in the bubbling fluidized bed grow in diameter.

Larger diameter particles (of silicon product) are removed from the FBR through the product withdrawal tube. Alternatively, all, or a portion of, the hydrogen may be fed into the FBR through the product withdrawal tube, e.g., countercurrent to the product exiting the FBR. Without wishing to be bound by theory, it is thought that feeding all, or a portion, of the hydrogen into the FBR through the product withdrawal tube may strip residual silicon bearing source gas from the larger diameter particles exiting the FBR. Adjustments of the hydrogen flow can also act to encourage segregation of smaller or undersized particles within the population from leaving the reactor system prematurely. However, it is recognized that the outflow of particles must be managed under the constraints of the particle population balance and bed inventory control strategies which maintain a stable particle size distribution that avoids significant fluctuations in reactor wall temperatures resulting from changing bed/wall heat transfer coefficients.

Heat may be added through the FBR walls to elevate the temperature of the particles, the silicon bearing source gas, and the hydrogen, so as to support reactions causing the thermal decomposition of the silicon monomer in the silicon bearing source gas to silicon that is deposited on the particles in the bubbling fluidized bed. Effluent gas leaves the top of the reactor through the gas outlet in the head of the FBR.

The silicon bearing source gas comprises a silicon monomer. The silicon bearing source gas may comprise chlorosilanes. The silicon bearing source gas may comprise $HSiCl_3$. Alternatively, the silicon bearing source gas may comprise $HSiCl_3$ and $SiCl_4$. When the silicon bearing source gas comprises $HSiCl_3$, the temperature in the FBR may range from 900° C. to 1250° C. Alternatively, the silicon bearing source gas may comprise $SiH_4$. When the silicon bearing source gas comprises $SiH_4$, the temperature in the FBR may range from 650° C. to 950° C.

The pressure in the FBR may range from 1 to 15 atmospheres (101.3-1520 kPa). Gas flow rates for the silicon bearing source gas and hydrogen are selected such that superficial velocity should be greater than minimum fluidization velocity, to aid bed turnover and minimization of segregation in the tapered section, and the gas velocity should typically be more than 30% higher than minimum fluidization velocity. For example, in operation at 45 psig (412 kPa) with chlorosilanes as the silicon bearing source gas at a temperature ranging from 950° C. to 1020° C., superficial velocity should be greater than 2 ft/s (0.61 m/s) for silicon particles having a Sauter mean particle size of 1320 micrometers.

When the gas distributor, described above, further comprises a plurality of gas inlets between the feed inlets and the outer edge of the gas distributor, then an etching gas may be fed into the FBR through these gas inlets. The etching gas may comprise HCl. Alternatively, the etching gas may comprise $SiCl_4$. The etching gas may be fed concurrently when the silicon bearing source gas is fed, according to the process described in U.S. Pat. No. 7,927,984 B2, which is hereby incorporated by reference to describe the process for minimizing deposition of silicon on the gas distributor and/or the walls of the FBR using a sufficient amount of etching gas to etch deposits from the internals of the FBR without substantially decreasing yield of product produced.

Figure 2:
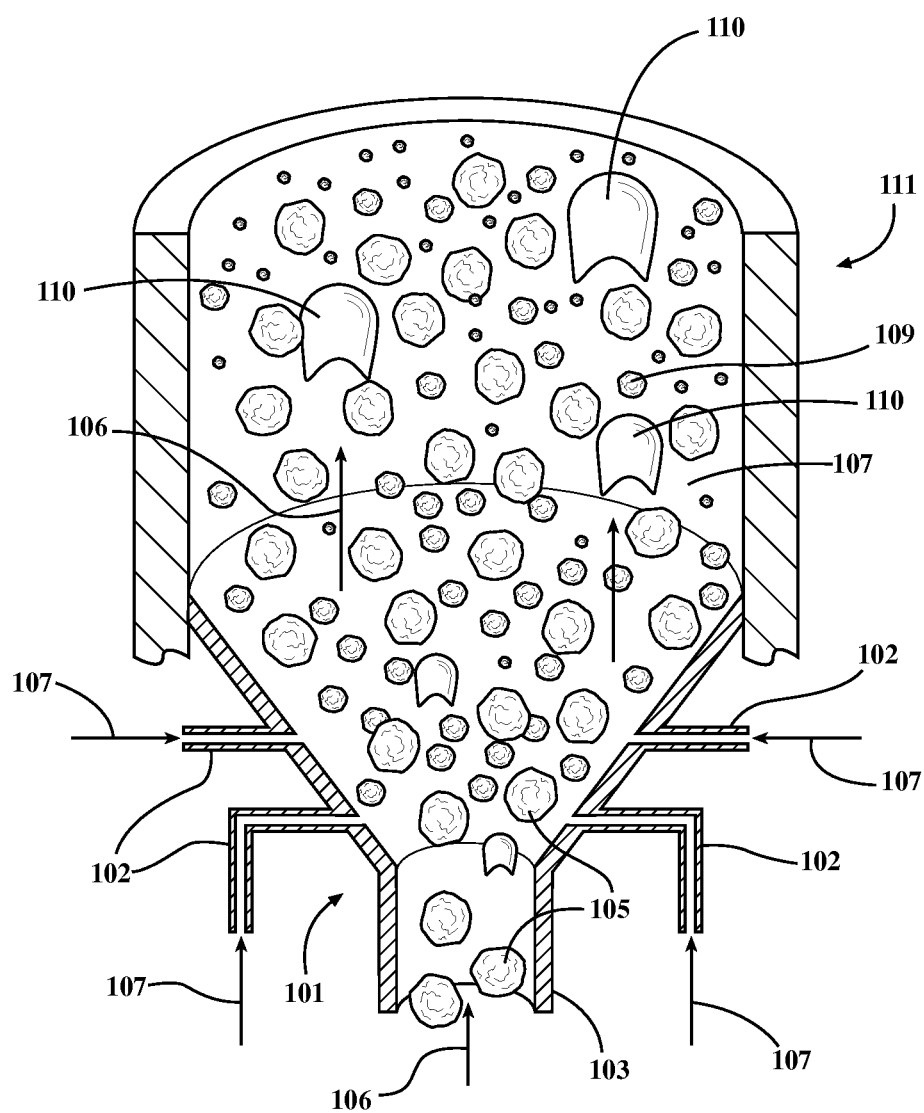
FIG. 2 shows an enlarged cross section of a conical gas distributor 101A suitable for use in the FBR 100 shown in FIG. 1.

FIG. 1 shows a schematic of a cross section of a FBR 100. The FBR 100 comprises a conical gas distributor 101A. FIG. 2 shows an enlarged cross section of the conical gas distributor 101A. The conical gas distributor 101A includes feed inlets 102 located between a product withdrawal tube 103 and the top edge 104 of the gas distributor 101A. Larger diameter particles (e.g., Geldart Group D) of silicon (product) 105 exit the FBR 100 through the product withdrawal tube 103. Hydrogen gas 106 is fed into the FBR 100 through the product withdrawal tube 103 countercurrent to the larger diameter particles of silicon 105 exiting the FBR 100. A silicon bearing source gas 107 is fed into the FBR 100 through feed inlets 102.

Immediately above the conical gas distributor 101A is a lower straight section 111 of the fluidized bed reactor 100. Segregation of larger diameter particles of silicon (product) 105 from smaller diameter particles (e.g., seed and intermediate) 109 occurs in the lower straight section 111. Above the lower straight section 111, is a tapered section 112 of the FBR 100. A bubbling fluidized bed 108 of silicon particles 109 and gas bubbles 110 resides in the lower straight section 111 and the tapered section 112. The tapered section 112 expands upward and outward in a cone shape. The cone angle 113 may range from 2.5° to 10° from vertical.

Above the tapered section 112, the FBR has an expanded head 114. The expanded head 114 is wider in diameter than the top 115 of the tapered section 112. Silicon particles 116

(e.g., seed particles used as a raw material, with smaller diameters than the product) are fed into the FBR 100 through a feed port 117 on top of the expanded head 114. A vent gas 118 exits the FBR 100 through a vent 119 on top of the expanded head 114. The vent gas 118 may comprise unreacted silicon bearing source gas and hydrogen, by products and/or silicon dust.

Figure 3:
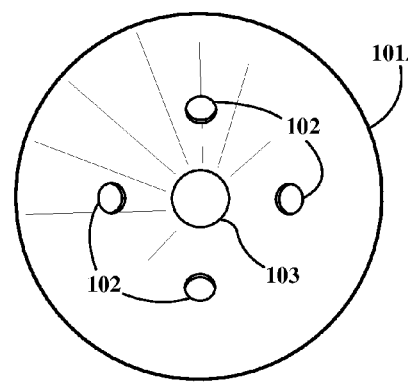
FIG. 3 shows a top view of the conical gas distributor 101A shown in FIG. 2.

FIG. 3 shows a top view of the conical gas distributor 101A that can be used in the FBR 100 shown in FIGS. 1 and 2. The conical gas distributor 101A has a product withdrawal tube 103 mounted in the center, i.e., at the lowest point. Feed gas inlets 102 surround the product withdrawal tube 103.

Figure 4A:
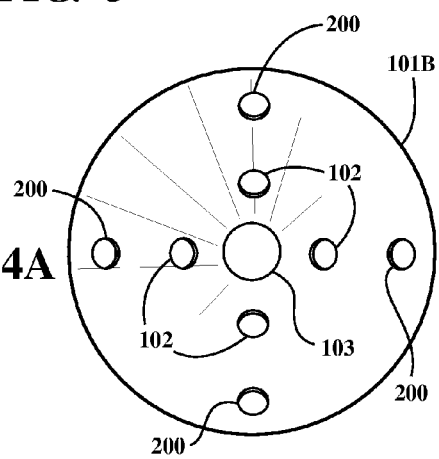
FIG. 4A shows a top view of an alternative conical gas distributor 101B suitable for use in the FBR 100 shown in FIG. 1.
Figure 4B:
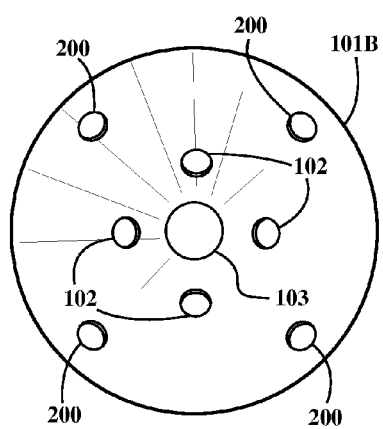
FIG. 4B shows a top view of another alternative conical gas distributor 101B suitable for use in the FBR 100 shown in FIG. 1.
Figure 4C:
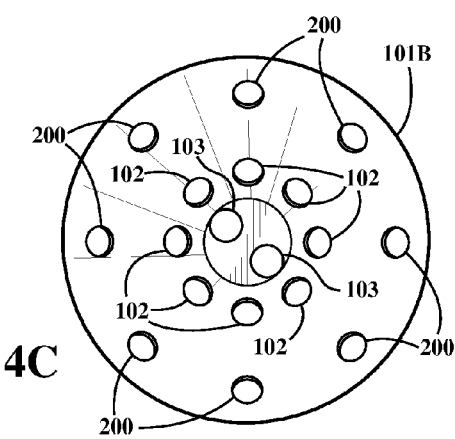
FIG. 4C shows a top view of yet another alternative conical gas distributor 101B suitable for use in the FBR 100 shown in FIG. 1.

FIGS. 4A, 4B, and 4C each show a top view of an alternative conical gas distributor 101B that can be used in the FBR 100 shown in FIGS. 1 and 2. The alternative conical gas distributor 101B can have one or more product withdrawal tubes 103 mounted in the center, i.e., in the lowest portion of the conical gas distributor 101, as shown in FIG. 4C. Feed gas inlets 102 surround the product withdrawal tube 103. Etch gas inlets 200 are located between the feed gas inlets 102 and the outer edge 201 of the conical gas distributor 101B.

Figure 5:
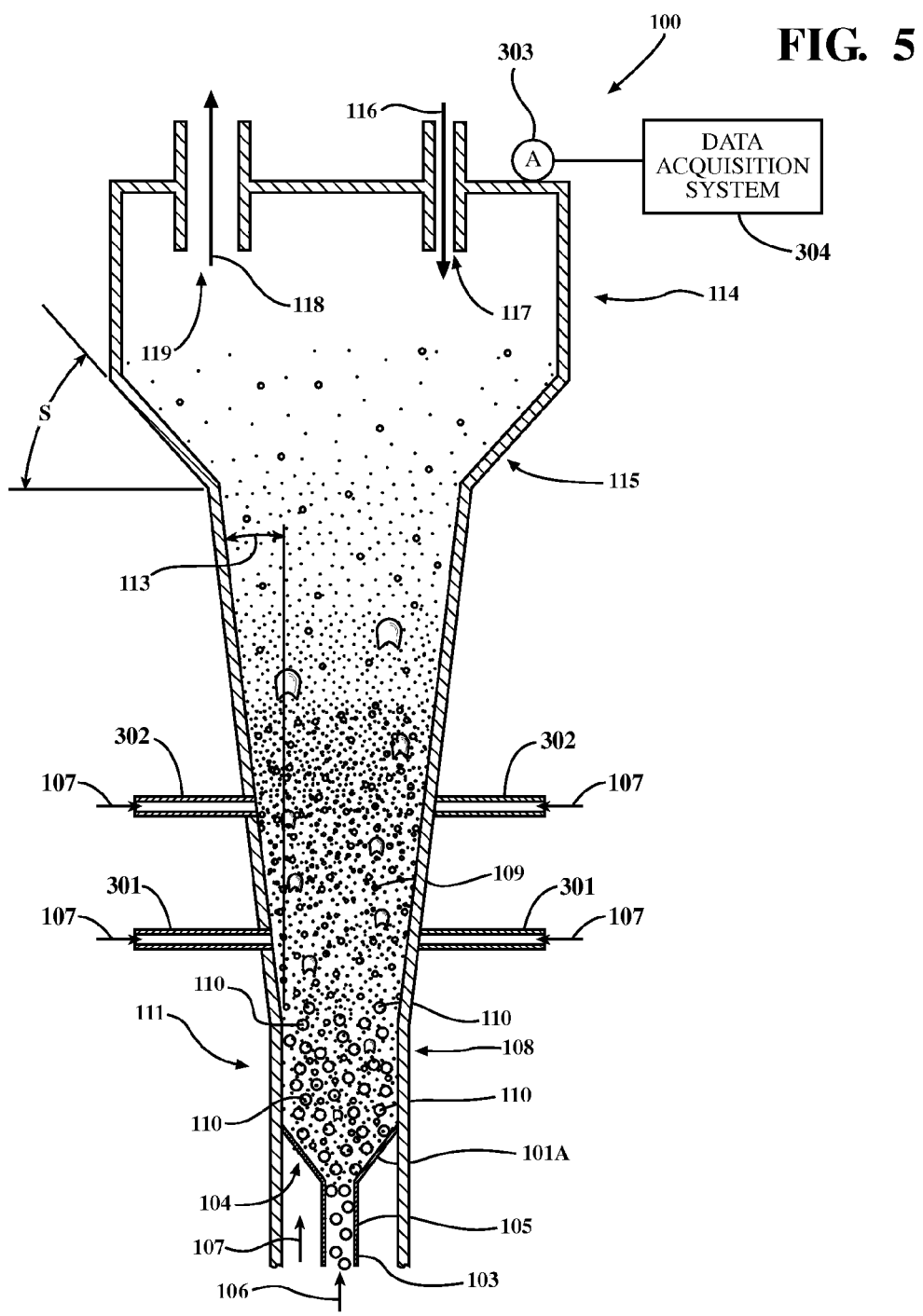
FIG. 5 shows a cross section a fluidized bed reactor having higher bed inventory with supplemental gas injection points 301 and 302 and an accelerometer 303.

With reference to FIG. 5, the fluidized bed reactor may include at least one row of gas injection ports defined by the tapered section 112. For example, as shown in FIG. 5, secondary gas inlets 301 and 302 are defined by the tapered section 112. The secondary gas inlets 301 and 302 can be used to introduce gases into the tapered section 112 of the FBR 100. The gasses are typically selected from the group of supplemental fluidizing gas, additional feed gas, etching gas, or diluents gas. However, it is to be appreciated that any type of gas may be introduced into the tapered section 112 through the secondary gas inlets 301 and 302.

The FBR 100 may further include an accelerometer 303 coupled to the FBR 100 for measuring vibrations of the FBR 100. The accelerometer 303 is typically attached to the FBR 100 at a location that protects the accelerometer from temperatures reached within the FBR 100 (maximum 650° C. for commercially available accelerometers). Alternatively, the accelerometer 303 may be adequately cooled locally to meet temperature limitations of the accelerometer 303. An example of a suitable accelerometer 303 is an Inconel®-jacketed high temperature piezoelectric accelerometer. Signals relating to the vibration of the FBR 100 measured by the accelerometer 303 are sent to a data acquisition system 304 where post processing of the acoustic signals can be used to interpret particle size. It is to be appreciated that protected coaxial cable with Inconel® jacketing may be used to transmit the signals from the accelerometer 303 to the data acquisition system 304.

The data acquisition system 304 can be used to process the signals received from the accelerometer 303. Typically, the signals sent by the accelerometer are acoustic signals relating to the vibration of the FBR 100. It is to be appreciated that measurements of the vibrations of the FBR 100 may be completed by conducting acoustic power spectrum analyses. Without wishing to be bound by theory, the position of the accelerometer is ideally in the vicinity of the bed upper surface where the bubbles within the FBR 100 are breaking so as to improve a signal-to-noise ratio of the acoustic signals. Based on the signals received by the data acquisition system 304, the Sauter mean particle size distribution within the FBR 100 can be calculated. More specifically, the signals relating to the vibration of the FBR 100, when coupled with superficial velocity of gas flowing through the FBR 100, and a bed inventory data (bed mass of particles within the FBR 100) can be used to determine the Sauter mean particle size (diameter) distribution within the FBR 100. For instance, in operation, bed mass can be estimated from an overall bed pressure drop or a nuclear level (gamma ray) gauge. Additionally, the superficial velocity can be directly calculated from flow measurements at the injection points and average gas molar volume, which can be calculated from equations of state given pressure and temperature data, both of which can be measured. Without being bound by theory, it is believed that statistical models can be employed to determine the Sauter mean particle size distribution of a fluidized bed based on the bed mass, the superficial velocity, and the vibration of the FBR 100.

The FBR and process described herein may be used in conjunction with other equipment and/or processes. For example, the FBR described herein may be used in the integrated fluidized bed reactor process of U.S. Pat. No. 7,935,327 B2, in which a vent gas leaving one or more Siemens reactors is used as all, or a portion, of the silicon bearing source gas fed into the bubbling fluidized bed in the tapered section of the FBR described herein.

EXAMPLES

These examples are intended to illustrate some embodiments of the invention and should not be interpreted as limiting the scope of the invention set forth in the claims. Reference examples should not be deemed to be prior art unless so indicated.

A pilot FBR is prepared to produce large steady-state silicon beads. The pilot FBR comprises a fluidized bed made from a cylindrical tube having an 8-inch (20.32 cm) inner diameter. An expanded head having an 18-inch (45.72 cm) inner diameter is coupled to one end of the fluidized bed. A gas distributor is coupled to another end of the fluidized bed grid. The gas distributor contains a plurality of holes for introducing a silicon bearing source gas into the fluidized bed. A discharge tube is defined at a bottom of the fluidized bed for discharging the large steady-state silicon beads. The fluidized bed is loaded with seed particles of silicon. During operation of the pilot FBR, silicon is deposited on the seed particles such that the seed particles grow in diameter. Silicon is deposited on the bed particles until the surface-to-volume mean diameter of the bed particles falls within the Geldart Group D classification and the average particle size distribution is maintained within an acceptable range based on the balance of seed addition rate to product withdrawal rate. As such, the pilot FBR is capable of fluidizing a population of particles falling with the Geldart Group D classification. Therefore, it is desirable to scale-up the pilot FBR for commercial production of large steady-state silicon beads. To facilitate this, validation studies on the bed hydrodynamics using principles of fluidization hydrodynamic scaling as described by Horio et al. (see "A New Similarity Rule for Fluidized Bed Scale-Up", *AIChE Journal*, 32:1466 (1986)). The scaled beds for the prescribed geometry were tested with model representatives under hydrodynamically equivalent operating conditions using air as the fluidizing gas to those in a chlorosilane-based deposition process. During the experimentation, accelerometer and differential pressure measurement devices were used to help characterize bed behavior. A critical aspect for the acquisition of pressure fluctuation data is that the pressure measurement device be fast acting relative to the bed frequencies (which are usually below 10 Hz), and the conduits connecting the process to the pressure measurement device be small enough that the vapor volume within the conduit does not act as dampening reservoir, which will result in false low measurements of the real pressure fluctuations. To alleviate this problem, conduit size is not recommended to be larger than 0.25-in (6.35 mm) diameter nominal.

The baseline model bed was constructed from plexiglass, which allowed for visual analysis of the bed behavior, in addition to pressure measurements. Air at atmospheric pressure was used as the fluidizing gas to simulate a fluidized bed at elevated pressure and elevated temperature (approximately 1000° C.) containing a mixture of chlorosilanes and hydrogen. The differential pressure above the grid section is monitored with differential pressure transmitters capable of sampling at 1 kHz rate. The differential pressure transmitters were spanned over a distance of 1 ft (30.48 cm). Each pressure tap was purged and tubing from the pressure tap location to the instrument was specified at 0.125-in. (3.175 mm) nominal diameter. The differential pressure drop was monitored during various conditions of fluidization at 1 kHz sample frequency, and the standard deviation of the differential pressure was calculated over a time averaged period of 60 seconds. The fluidized bed of baseline model FBR is loaded with particles falling within the Geldart Group B and Geldart Group D classifications with the average particle size distribution falling into Geldart Group D (Sauter mean=1515 micrometers). Pressure fluctuations were monitored for several different superficial velocities and two bed inventories. When the standard deviation of differential pressure exceeded 5 inches of water (1.25 kPa), the bed was observed to slug.

A first scaled-up FBR model system is prepared. The first scaled-up FBR comprises a fluidized bed made from a steel cylindrical tube having a 36-inch (91.1 cm) nominal diameter (inner diameter=35.25 inches (89.53 cm)). A conical gas distributor is attached at one end of the fluidized bed of the first scaled-up FBR. The gas distributor of the first scaled-up FBR contains a plurality of holes for introducing air into the fluidized bed. The differential pressure above the grid section is monitored with differential pressure transmitters capable of sampling at 1 kHz rate. The differential pressure transmitters were spanned over a distance of 2 ft (60.96 cm). Each pressure tap was purged and tubing from the pressure tap location to the instrument was specified at 0.125-in. (3.175 mm) nominal diameter. The differential pressure drop was monitored during various conditions of fluidization at 1 kHz sample frequency, and the standard deviation of the differential pressure was calculated over a time averaged period of 60 seconds. The fluidized bed of the first scaled-up FBR is loaded with particles falling within the Geldart Group B and Geldart Group D classifications. Two different mixtures having different Sauter mean particle sizes were tested (730 micrometers—Geldart B and 1524 micrometers—Geldart D). During operation of the first scaled-up FBR, gas bubbles grow to a very large diameter very quickly, which resulted in severe slugging and mechanical vibration of the vessel. Despite being considerably larger in diameter than the 8-in. (20.32 cm) base case which allows for bigger bubble growth without wall constraints, slugging was observed when the standard deviation of pressure exceeded 6 inches of water (1.49 kPa). A height of the fluidized bed is varied to reduce the slugging caused by the gas bubbles. A non-slugging height of the fluidized bed of the first scaled-up FBR is identified for each particle size and the non-slugging height of the smaller particles exceeds that for the larger particles. However, the non-slugging height of the fluidized bed of the first scaled-up FBR is too shallow to allow for the proper amount of reactor wall heating needed to achieve process temperatures that would allow controlled chemical vapor deposition of silicon on particles within the fluidized bed. Therefore, further considerations to gas bubble development must be considered in order to scale-up the pilot FBR.

A second scaled-up FBR is prepared. The second scaled-up FBR comprises a fluidized bed made from a tapered-wall plexiglass tube having an 8-inch (20.32 cm) diameter at one end and expanding to a 15.5-inch (39.37 cm) diameter at the other end. A conical gas distributor is attached at the 8-inch (20.32 cm) diameter end of the fluidized bed of the second scaled-up FBR. The gas distributor of the second scaled-up FBR contains a plurality of holes for introducing gas into the fluidized bed. The differential pressure above the grid section is monitored with differential pressure transmitters capable of sampling at 1 kHz rate. The differential pressure transmitters were spanned over a distance of 1 ft (30.48 cm). Each pressure tap was purged and tubing from the pressure tap location to the instrument was specified at 0.125-in. (3.175 mm) nominal diameter. The differential pressure drop was monitored during various conditions of fluidization at 1 kHz sample frequency, and the standard deviation of the differential pressure was calculated over a time-averaged period of 60 seconds. The fluidized bed of the second scaled-up FBR is loaded with particles falling within the Geldart Group B and Geldart Group D classifications with the average particle size distribution falling into Geldart Group D (Sauter mean=1515 micrometers). During operation of the second scaled-up FBR, gas bubbles growth is limited in size. Slugging was not observed, and the time averaged standard deviation of differential pressure was below 5 inches of water (1.25 kPa).

A third scaled-up FBR is prepared. The third scaled-up FBR comprises a fluidized bed made from a tapered-wall plexiglass tube having a 17.5-inch (44.45 cm) diameter at one end and expanding to a 40-inch (101.6 cm) diameter at the other end. A conical gas distributor is attached at the 17.5-inch (44.45 cm) diameter end of the fluidized bed of the third scaled-up FBR. The gas distributor of the third scaled-up FBR contains a plurality of holes for introducing gas into the fluidized bed. The differential pressure above the grid section is monitored with differential pressure transmitters capable of sampling at 1 kHz rate. The differential pressure transmitters were spanned over a distance of 1 ft (30.48 cm). Each pressure tap was purged and tubing from the pressure tap location to the instrument was specified at 0.125-in. (3.175 mm) nominal diameter. The differential pressure drop was monitored during various conditions of fluidization at 200 Hz sample frequency, and the standard deviation of the differential pressure was calculated over a time averaged period of 60 seconds. An accelerometer (Model: Kistler K-Shear 8712A5M1) was also placed on the vessel at a distance of 56 inches (142.24 cm) above the top of the gas distributor, and this device was coupled to a data acquisition system to acquire and process the acoustical signals. The standard deviation of the accelerometer signal was also calculated over a time averaged period of 60 seconds. The fluidized bed of the third scaled-up FBR is loaded with particles falling within the Geldart Group B and Geldart Group D classifications. Two different particle size distributions were tested, one having a Sauter mean diameter of 974 micrometers and a second having a Sauter mean diameter of 1263 micrometers. During operation of the third scaled-up FBR, gas bubbles growth is limited in size compared with the second scaled-up FBR. Slugging was not observed for the 974 micrometer particle size distribution and the standard deviation of differential pressure went as high as 10 inches of water (2.49 kPa). For the 1263 micrometer mixture, slugging was observed when the standard deviation of pressure fluctuations exceeded 7 inches of water (1.74 kPa).

A fourth scaled-up FBR is prepared. The fourth scaled-up FBR comprises a fluidized bed made from a tapered-wall tube having a 17.5-inch (44.45 cm) diameter at one end and expanding to a 40-inch (101.6 cm) diameter at the other end. A conical gas distributor is attached at the 17.5-inch (44.45 cm) diameter end of the fluidized bed of the fourth scaled-up FBR. The gas distributor of the fourth scaled-up FBR contains a plurality of holes for introducing gas into the fluidized bed. A second set of gas injection nozzles is placed within the tapered section at an elevation of 62 inches (157.48 cm) above the top of the gas distribution plenum. The differential pressure above the grid section is monitored with differential pressure transmitters capable of sampling at 1 kHz rate. The differential pressure transmitters were spanned over a distance of 1 ft (30.48 cm). Each pressure tap was purged and tubing from the pressure tap location to the instrument was specified at 0.125-in. (3.175 mm) nominal diameter. The differential pressure drop was monitored during various conditions of fluidization at 200 Hz sample frequency, and the standard deviation of the differential pressure drop was calculated over a time averaged period of 60 seconds. An accelerometer (Model: Kistler K-Shear 8712A5M1) was also placed on the vessel at a distance of 56 inches (142.24 cm) above the top of the gas distributor, and this device was coupled to a data acquisition system to acquire and process the acoustical signals. The standard deviation of the accelerometer signal was also calculated over a time averaged period of 60 seconds.

The fluidized bed of the fourth scaled-up FBR is loaded with particles falling within the Geldart Group B and Geldart Group D classifications. Gas flows to both the primary distributor and the second set of nozzles were controlled. During operation of the fourth scaled-up FBR, gas bubbles growth is further limited in size for both particle size distributions by adding gas to the upper nozzles while holding total gas flow constant. The addition of gas to secondary nozzles shows a clear benefit with respect to total gas throughput without reduction in bed stability. Table 1 shows the response of the standard deviation of pressure fluctuations as a result of increasing the gas flow in the second set of nozzles while holding the gas flow to the inlet distributor constant at 330 scfh (0.934 m³/hr) air flow. Bed inventory was held at 1932 lb (876.3 kg) of silicon beads having a 1263 micrometer Sauter mean particle size.

TABLE 1

| Percentage Increase of Total Volumetric Flow through Secondary Gas Injection Above Fixed Baseline Flow from Primary Gas Distributor Location | Time-Averaged Standard Deviation of Differential Pressure (kPa) |
| --- | --- |
| 0% | 1.69 |
| 19% | 1.27 |
| 29% | 1.39 |

Slugging was not observed for the 974 micrometer particle size distribution in the fourth scaled up FBR, and pressure fluctuations were lower than the third scaled up FBR for the same inventory and total gas flow rate. Slugging was also not observed for the 1263 micrometer particle size distribution over the range of velocities tested.

Table 2 depicts a comparison of the vibrations (acceleration measurements) of the fourth scaled up FBR for the two particle size distributions. For a fixed bed inventory (2919 lb (1324 kg)), the accelerometer showed that the 1263 micrometer Sauter mean particle size distribution had higher vibrational activity than a 974 micrometer Sauter mean particle size distribution at each gas superficial velocity. Thus, unlike previous uses of accelerometers for determining bed density, it has been identified that acceleration measurements characterizing the vibration of the fourth scaled up FBR measured by the accelerometer can be used for determining particle size distribution when coupled with superficial velocity and bed inventory (bed mass) data. Again, without being bound by theory, it is believed that statistical models can be employed to determine Sauter mean particle size distributions of a fluidized bed based on vibrations of the FBR, bed mass, and superficial velocity inputs.

TABLE 2

| Sauter Mean Particle Size (micrometers) | Superficial Velocity at the 17.5 in. (44.45 cm) Diameter Datum (m/s) | Time-Averaged Standard Deviation of Acceleration (m/s²) |
| --- | --- | --- |
| 974 | 0.591 | 0.56 |
| 974 | 0.796 | 0.71 |
| 1263 | 0.582 | 0.58 |
| 1263 | 0.735 | 0.89 |

Without being bound by theory, it is believed that the fluidized bed made from a tapered tube such as that disclosed in the second, third, and fourth scaled-up fluidized bed reactor examples prevents the fast growth of small gas bubbles into a fewer larger bubbles by reducing the excess gas velocity within the bubble phase in the upper portion of the fluidized bed, which allows some of the smaller gas bubbles to be routed into the emulsion phase. This prevents the gas bubbles from growing larger by coalescence. It is also believed that the fluidized bed made from the tapered-wall tube promotes motion of the emulsion phase solids along the tapered-wall of the fluidized bed, which leads to good scouring of the tapered-wall and prevents any build-up of agglomerates. Additionally, the design of the tapered wall of the fluidized bed allows gas introduction at multiple axial locations throughout the tapered wall. If the local fluidization superficial velocity drops below the minimum fluidization velocity due to the growth of the bed cross-section, the addition of gas allows for sustainable fluidization at those bed heights. Also, as disclosed in the fourth scaled-up fluidized bed reactor example, the staging of the gas injection allows for net increase in the gas throughput across the reactor unit by limiting the onset of slugging in the lower section of the reactor.

INDUSTRIAL APPLICABILITY

The inventors surprisingly found that particles classified in Geldart Group B and Geldart Group D can be produced in a deep bubbling fluidized bed using a tapered FBR that is not spouted or small diameter (less than 8 inches (20.32 cm)). The fluidization behavior had reduced pressure fluctuations compared with a fluidized bed reactor with a cylindrical body. The tapered FBR and process are useful for manufacturing polycrystalline silicon.

The invention claimed is:
1. A fluidized bed reactor comprising:
    a conical gas distributor having a top edge,
    a product withdrawal tube mounted to the gas distributor,
    a plurality of feed inlets defined by the conical gas distributor between the top edge and the product withdrawal tube;

a tapered section above the conical gas distributor, where the tapered section of the fluidized bed reactor expands upward and outward from the top edge of the conical gas distributor; and an expanded head above the tapered section, wherein a diameter of the expanded head is larger than a diameter of the tapered section; and wherein the slope of the expanded head with respect to the horizontal plane of the transition point is at least 40 degrees.

2. The fluidized bed reactor of claim 1, further comprising at least one straight section selected from:

a lower straight section located above the conical gas distributor and below the tapered section, an upper straight section located above the tapered section and below the expanded head, or both the lower straight section and the upper straight section.

3. The fluidized bed reactor of claim 1, where the tapered section expands upward and outward at a cone angle ranging from 2.5° to 10.0° from vertical.

4. The fluidized bed reactor of claim 1, further comprising a plurality of gas inlets, where the gas inlets are defined by the conical gas distributor, and the gas inlets are located between the feed inlets and the top edge of the conical gas distributor.

5. The fluidized bed reactor of claim 1, further comprising a heater oriented to the fluidized bed reactor, so as to provide heat to the tapered section when the heater operates, a supplemental heater oriented to the fluidized bed reactor so as to provide heat at the conical gas distributor when the supplemental heater operates, and a straight section heater oriented to the fluidized bed reactor, so as to provide heat to the at least one straight section when the straight section heater operates.

6. The fluidized bed reactor of claim 1, further comprising a bubbling fluidized bed comprising Geldart Group D particles residing at least in part in the tapered section, where the particles are silicon particles.

7. The fluidized bed reactor of claim 6, further comprising an accelerometer coupled to the fluidized bed reactor for measuring vibrations of the fluidized bed reactor to determine a Sauter mean particle size distribution of the particles.

8. A fluidized bed reactor of claim 1, further comprising at least one row of gas injection ports defined by the tapered section to add additional feed gas, etching gas or diluent gas.

* * * * *